US012728027B2

(12) United States Patent
Kamal

(10) Patent No.: US 12,728,027 B2
(45) Date of Patent: Sep. 8, 2026

(54) MULTIFUNCTIONAL DE QUERVAIN'S BRACE

(71) Applicant: Saba Kamal, San Jose, CA (US)

(72) Inventor: Saba Kamal, San Jose, CA (US)

( * ) Notice: Subject to any disclaimer, the term of this patent is extended or adjusted under 35 U.S.C. 154(b) by 0 days.

(21) Appl. No.: 19/022,851

(22) Filed: Jan. 15, 2025

(65) Prior Publication Data

US 2026/0199115 A1 Jul. 16, 2026

(51) Int. Cl.
*A61F 5/01* (2006.01)

(52) U.S. Cl.
CPC .................................. *A61F 5/0118* (2013.01)

(58) Field of Classification Search
CPC .... A61F 5/0118; A61F 5/013; A61F 5/05866; A61F 2005/0186; A61F 2007/023; A41D 13/081; A41D 19/01582; A41D 19/01588; A63B 71/141
USPC ........................................................... 602/22
See application file for complete search history.

(56) References Cited

U.S. PATENT DOCUMENTS 1,994,235 A * 3/1935 Solomon .................. A45C 3/02 190/902
4,584,993 A * 4/1986 Nelson .................. A61F 5/0118 D24/190
4,781,178 A * 11/1988 Gordon ................. A61F 5/0118 602/22
5,261,871 A * 11/1993 Greenfield ............ A61F 5/0109 602/19
5,267,943 A * 12/1993 Dancyger ............. A61F 5/0118 602/5
5,279,545 A * 1/1994 Reese, Sr. ............... A61F 5/013 602/21
5,415,624 A * 5/1995 Williams .................. A61F 7/02 602/14
5,513,657 A * 5/1996 Nelson .................. A61F 5/0118 602/20
5,759,166 A * 6/1998 Nelson .................. A61F 5/0118 602/21
5,819,313 A * 10/1998 McCrane ............... A63B 71/14 473/62
5,820,526 A * 10/1998 Hoffman .............. A63B 21/065 482/55
5,928,172 A * 7/1999 Gaylord ................ A61F 5/0118 602/21

(Continued)

*Primary Examiner* — Rachael E Bredefeld
*Assistant Examiner* — Kevin S Albers

(57) ABSTRACT

A multifunctional De Quervain's brace is an apparatus that changes the angle of pull of the tendons to provide some release in tension at the musculotendinous junction, thereby providing pain relief. The apparatus includes a thumb spica, insert-receiving pockets, and reinforcing inserts. The thumb spica corresponds to the main structure of the apparatus that is wrapped around the user's hand and wrist to position the insert-receiving pockets and the corresponding reinforcing inserts on the radial side of the thumb spica. The insert-receiving pockets and the reinforcing inserts enable the adjustment of the restriction of the user's hand movements for different activities. In addition, the apparatus can be arranged into a static configuration for low-movement activities, such as sleeping or lifting, or into a dynamic configuration for high-movement activities, such as exercising and other daytime activities while still receiving the benefit of the release at the musculotendinous junction.

13 Claims, 6 Drawing Sheets

(56) References Cited

U.S. PATENT DOCUMENTS

| | | | | |
|---|---|---|---|---|
| 6,024,715 | A * | 2/2000 | Maxwell | A61F 5/0118 602/21 |
| 6,240,604 | B1 * | 6/2001 | Fox | A44B 19/262 24/429 |
| 7,033,331 | B1 * | 4/2006 | Hely | A61F 5/0118 128/878 |
| 7,056,298 | B1 * | 6/2006 | Weber | A61F 5/0118 2/21 |
| 9,895,251 | B2 * | 2/2018 | Fried | A61F 7/02 |
| 10,368,594 | B1 * | 8/2019 | LaCroix | A41D 13/08 |
| 11,529,279 | B2 | 12/2022 | Maier | |
| 11,654,073 | B2 | 5/2023 | Maier | |
| 11,819,439 | B1 * | 11/2023 | Watabe | A61F 5/013 |
| 12,138,190 | B1 * | 11/2024 | Weber | A61F 5/0118 |
| 12,403,029 | B1 * | 9/2025 | Solotoff | A61F 5/0118 |
| 12,508,141 | B2 * | 12/2025 | Millet | A61F 5/0118 |
| 2007/0239093 | A1 * | 10/2007 | Wyatt | A61F 5/0118 602/12 |
| 2008/0287848 | A1 * | 11/2008 | Jaccard | A61F 5/05866 602/22 |
| 2008/0307559 | A1 * | 12/2008 | Wright | A63B 71/141 2/161.1 |
| 2009/0082708 | A1 * | 3/2009 | Scott | A61F 5/0118 602/36 |
| 2010/0000006 | A1 * | 1/2010 | Butler | A63B 71/141 2/160 |
| 2010/0081981 | A1 * | 4/2010 | Cheng | A61F 5/0118 602/21 |
| 2011/0283432 | A1 * | 11/2011 | Best | A41D 13/0012 2/16 |
| 2013/0211304 | A1 * | 8/2013 | Romo | A61F 5/0118 602/21 |
| 2015/0374528 | A1 * | 12/2015 | Mueller | A61F 5/0118 602/21 |
| 2016/0030222 | A1 * | 2/2016 | Collier | A61F 5/0113 602/27 |
| 2016/0128859 | A1 * | 5/2016 | Brandt | A63B 21/4017 602/63 |
| 2017/0014257 | A1 * | 1/2017 | Wellendorf | A61F 5/05866 |
| 2017/0143526 | A1 * | 5/2017 | Gaylord | A61F 5/0118 |
| 2018/0055672 | A1 * | 3/2018 | Erwin | A61F 5/0118 |
| 2019/0230999 | A1 * | 8/2019 | Bozelko | A41D 27/10 |
| 2020/0016009 | A1 * | 1/2020 | Colleran | A41D 13/0512 |
| 2020/0093628 | A1 * | 3/2020 | Sigurdsson | A43B 7/20 |
| 2021/0128336 | A1 * | 5/2021 | Broussard | A61F 5/0102 |
| 2024/0065726 | A1 | 2/2024 | Barnes et al. | |
| 2024/0382333 | A1 * | 11/2024 | Lu | A61F 5/0106 |

* cited by examiner

MULTIFUNCTIONAL DE QUERVAIN'S BRACE

FIELD OF THE INVENTION

The present invention relates generally to wearable medical devices. More specifically, the present invention discloses a novel De Quervain's brace that reduces wrist and thumb pain with rest and while performing daily activities.

BACKGROUND OF THE INVENTION

Repeated motion injuries to the wrist and/or thumb are a steadily increasing issue among workers who perform repetitive tasks, especially among typists and other keyboard operators. Motion injuries are prevalent in new mothers when performing daily tasks, such lifting the baby or breastfeeding, which can involve movements in extreme positions that result in tendon irritation. Other repetitive motion injuries associated with the thumb are caused by the constant use of portable computing devices such as cellphones and tablet computers. These injuries include, but are not limited to, Carpal Tunnel Syndrome (CTS), De Quervain's tenosynovitis, tendonitis, etc. The pain resulting from such injuries, arthritis, tendonitis, hand fatigue, and other issues can be excruciating, difficult to treat, debilitating and may result in surgeries which often result in loss of productivity. Loss of productivity due to these ailments and injuries among keyboard operators is estimated to be in the billions of dollars annually.

To help with the treatment of these ailments, several orthopedic restraint devices of different types and styles have been made commercially available. These restraint devices, of course, have various degrees of effectiveness by restraining some of the wrist/thumb movement. However, mere movement restraint does not address the pain and the angle of pull when the restraint device is removed which results in the recurrence of the ailments. Further, there is a countervailing need to accommodate some movement in a working environment to allow change of the angle of pull while simultaneously releasing the tissue to treat the problem. The orthopedic restraint devices must strike a compromise between maximum restraint and some mobility. In other words, the orthopedic restraint devices should provide comfort and retain a significant stiffness that will urge but not force the wearer's wrist and thumb to neutral positions. So, there is a need for an orthopedic restraint device that addresses these concerns and provides such restraint as well as movement while addressing the tissues release within acceptable medical parameters via adjustable comfort with a desirable degree of mobility.

Therefore, an objective of the present invention is to provide a multifunctional De Quervain's brace. The present invention enables the implementation of rigid and semi-rigid immobilization to modify the angle of pull on the muscles to relieve the pressure from the tendons while providing release. The present invention includes static and dynamic parts that can be arranged for low-movement tasks, such as sleeping or lifting, or for high-movement tasks, such as exercising or even typing. Further, the present invention includes means to safely pull on the tissue for the treatment within adjustable medical parameters by providing some release to the tissues. In addition, the present invention includes several adjustment features designed to receive a thermoplastic or metal insert to enable the adjustment of the movement restraint of the user's hand. The adjustment features include a hook-and-loop fastener that enables the control of the movement restraint of the user's hand. The movement restraint adjustment enables movement within adjustable medical parameters to treat repetitive stress injuries including De Quervain's tenosynovitis syndrome. Additional features and benefits of the present invention are further discussed in the sections below.

SUMMARY OF THE INVENTION

The present invention discloses a multifunctional De Quervain's brace that relieves pain symptoms and restricts movement of the user's hand for day and night wear through passive tissue stretch to the intersection area, thereby releasing the tissue and changing the angle of pull of the tendons. The present invention includes several insert-receiving pockets integrated into a neoprene thumb spica that receives the corresponding reinforcing inserts to restrict movement in a controller manner while simultaneously preventing excessive radial or ulnar deviation of the wrist. The present invention serves three functions: helps change the angle of pull on the tendons crossing the wrist, provides release of tension at the musculotendinous junction, and thereby provides pain relief with daily activities. The present invention includes a static arrangement that maintains neutral positioning of the wrist and thumb while also facilitating the release of tissues during low-movement actions, such as sleeping or lifting. The present invention also includes a dynamic arrangement that allows movement of the thumb with a modified angle of pull of the tendons, thus making the thumb movement pain free.

In the preferred embodiment, the thumb spica of the present invention accommodates the shape and fit of the patient's wrist and thumb. Each of the insert-receiving pockets receives a reinforcing insert, preferably a thermoplastic piece, on the radial (thumb) side of the brace. Further, each of the insert-receiving pockets includes a fastener on the corresponding opening that allows static positioning of the wrist when closed and movement when lifted. The fastener is preferably lined on each side with metal wiring to provide rigidity to maintain static positioning and limit movement. In addition, the metal wiring allows the fastener to be bendable to lift over to allow movement of the thumb. In addition, the present invention includes a neoprene hook-and-loop strap that spans from the volar radial side of the wrist on the inside of the brace and wraps on the dorsal aspect of the user's wrist while exiting out from the ulnar (pinky) side of the brace. Further, the underside of the hook-and-loop strap is lined with silicone which is also attached with a hook-and-loop fastener to the strap. The strap then wraps on the volar (front) side of the outside of the brace to attach just before the plurality of insert-receiving pockets. The brace can then be closed via an additional hook-and-loop fastener on the dorsal ulnar side of the wrist and forearm.

DETAILED DESCRIPTION OF THE INVENTION

All illustrations of the drawings are for the purpose of describing selected versions of the present invention and are not intended to limit the scope of the present invention.

Figure 1:
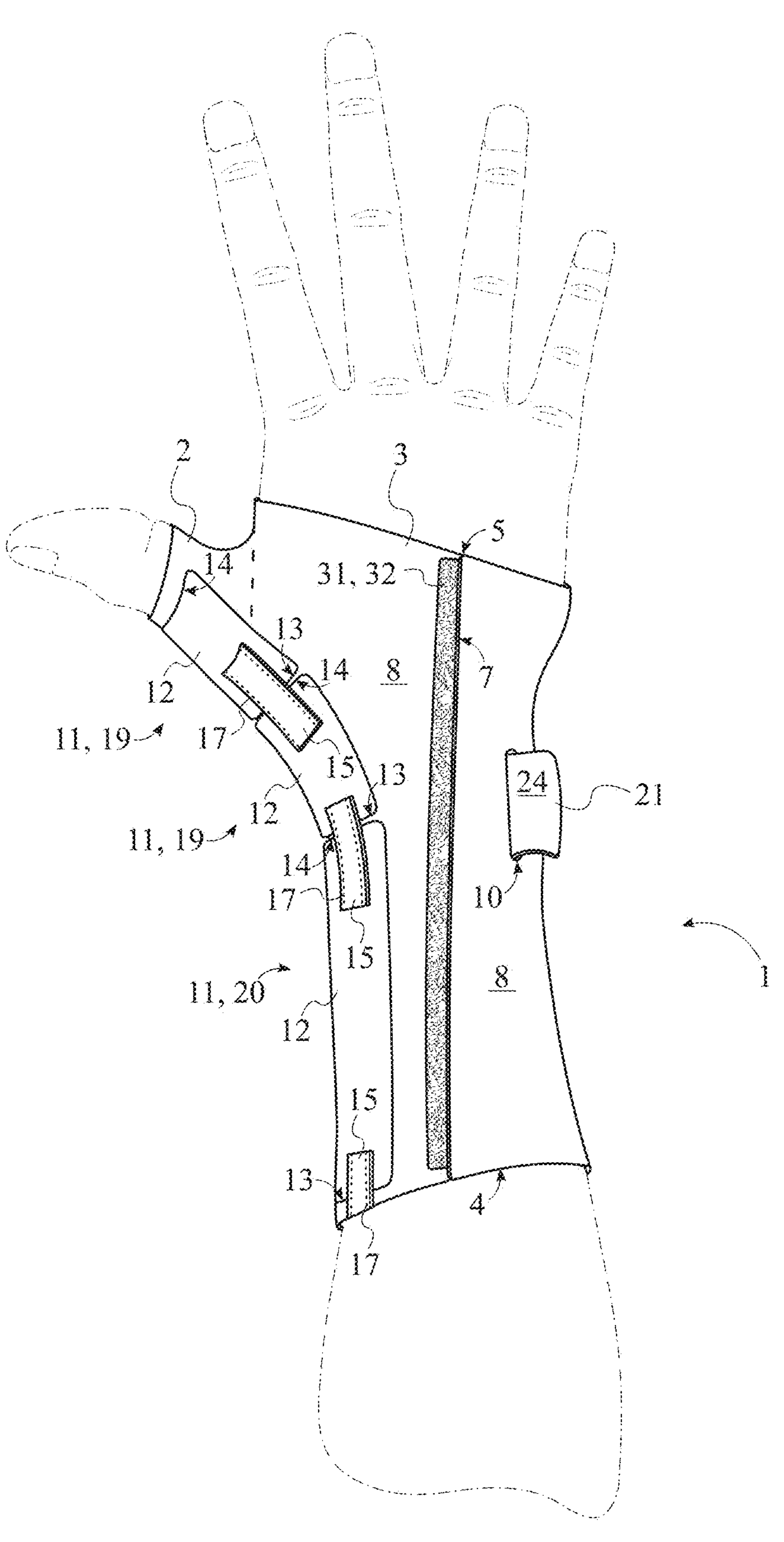
FIG. 1 is a top view of the present invention, wherein the present invention is shown fastened around the user's hand and wrists, and wherein the present invention is shown in a static configuration.
Figure 2:
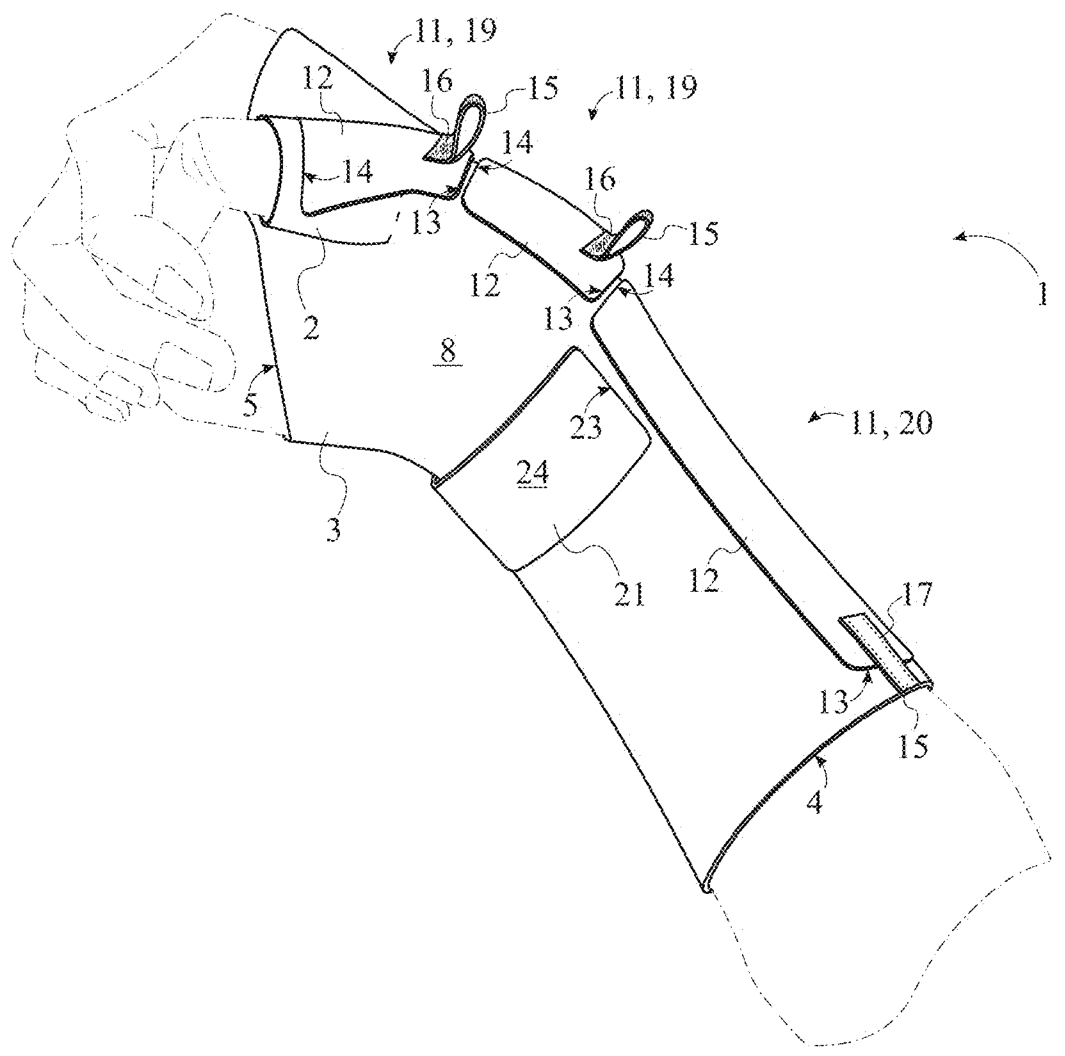
FIG. 2 is a bottom view of the present invention thereof, wherein the present invention is shown in a dynamic configuration.
Figure 3:
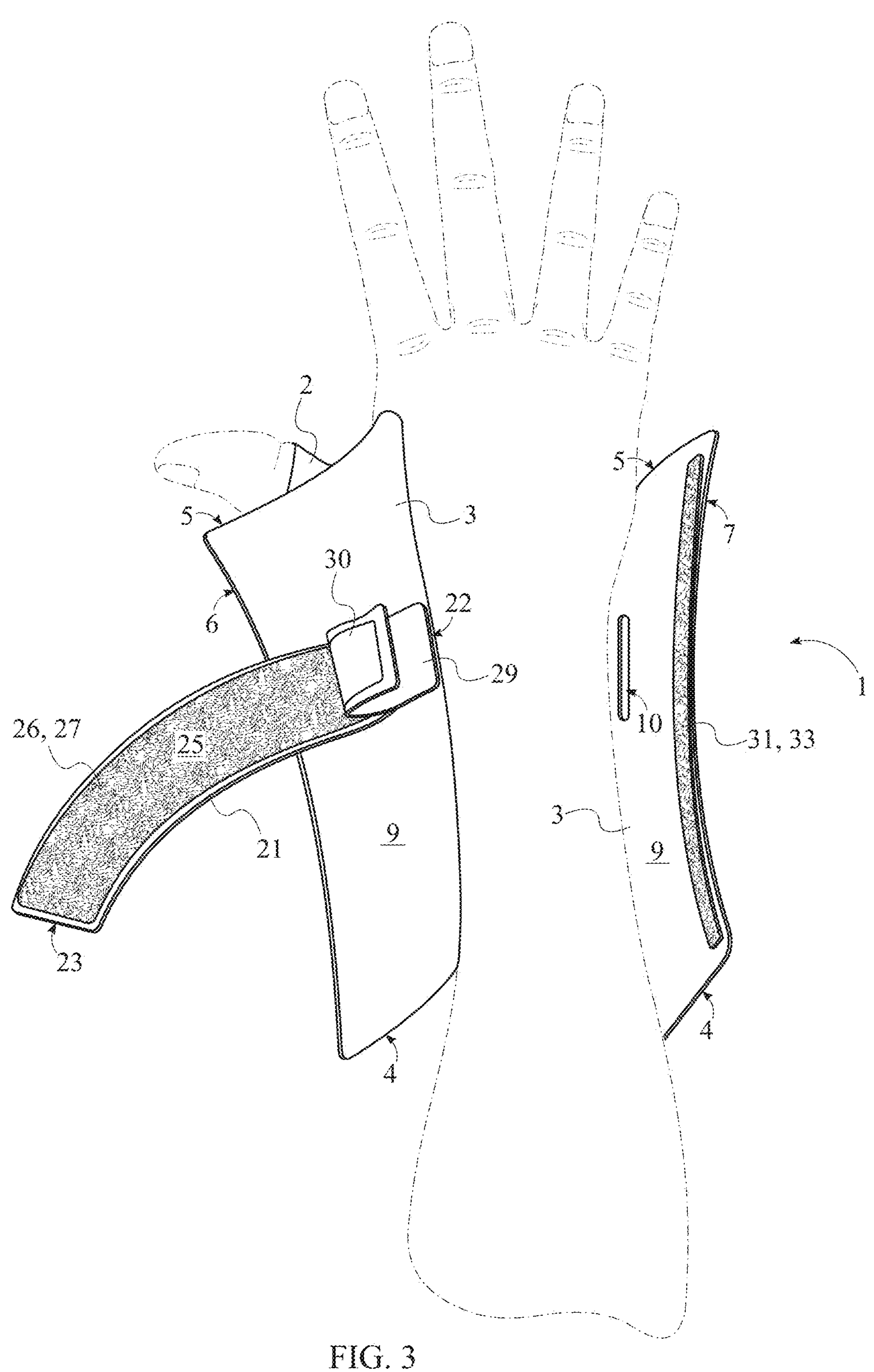
FIG. 3 is a top view of the present invention, wherein the present invention is shown being put on by inserting the user's thumb through the thumb sleeve and placing the wrist-bracing wrap around the user's hand and wrist.
Figure 4:
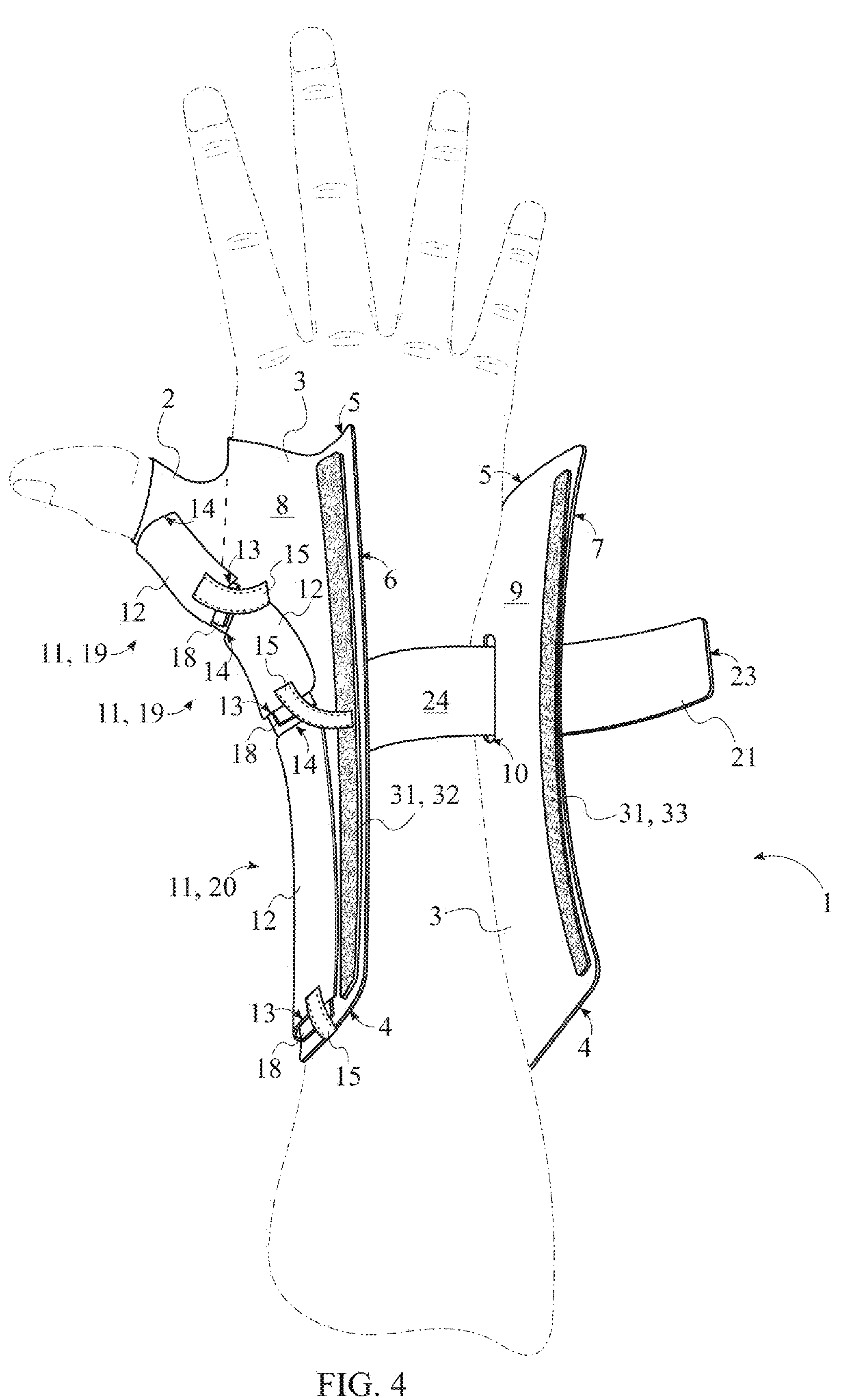
FIG. 4 is a top view of the present invention, wherein the wrist-bracing wrap is shown being fastened around the user's hand and wrist by looping the tightening strap through the strap opening.
Figure 5:
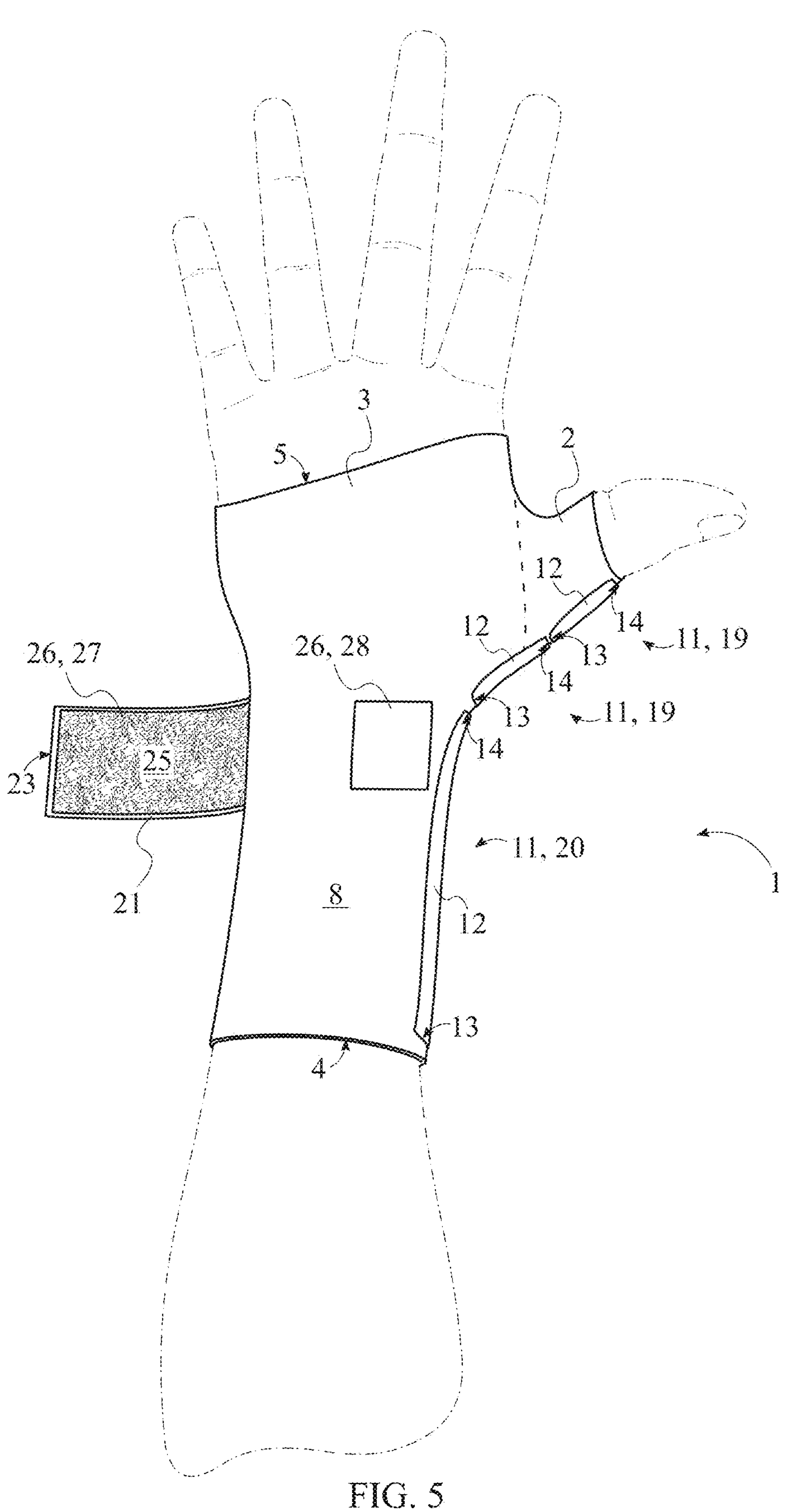
FIG. 5 is a bottom view of the present invention, wherein the wrist-bracing wrap is shown being fastened around the user's hand and wrist by wrapping the tightening strap around the user's wrist.
Figure 6:
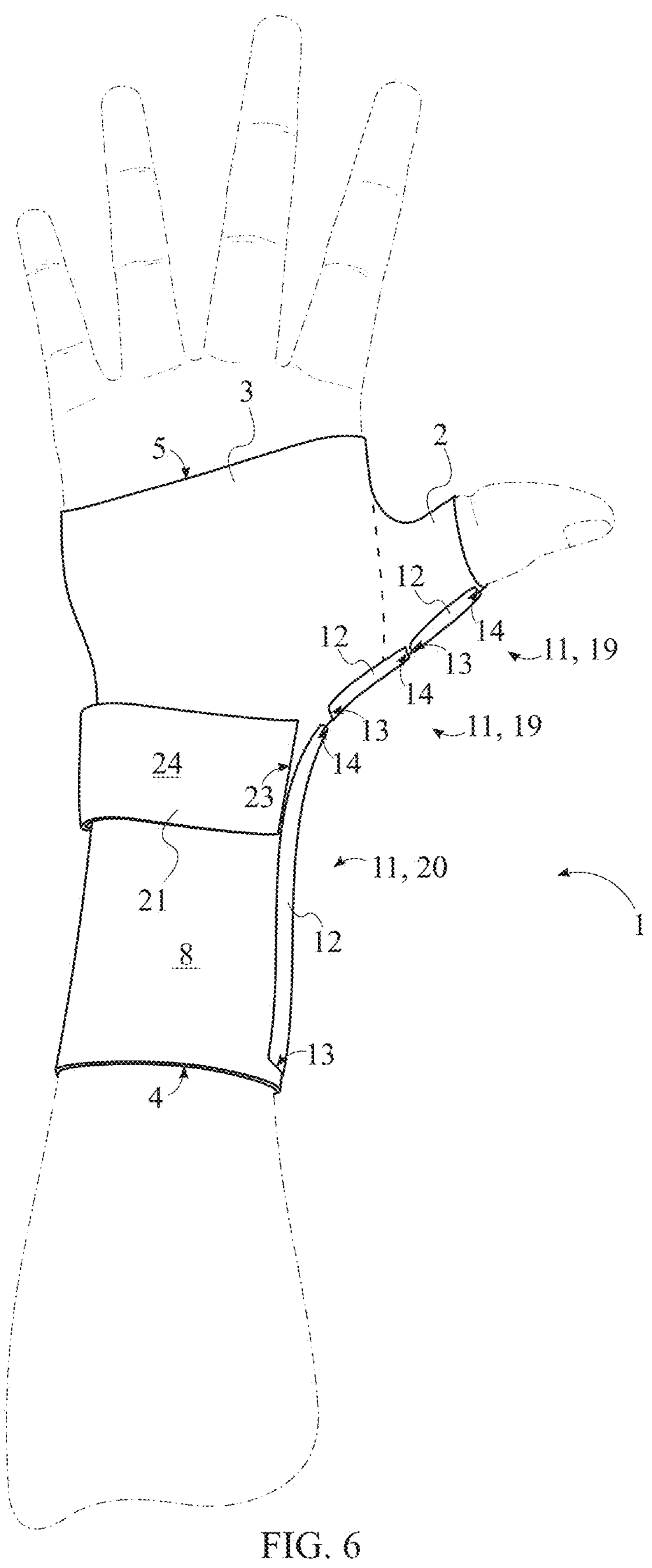
FIG. 6 is a bottom view of the present invention, wherein the wrist-bracing wrap is shown fastened around the user's hand and wrist by fastening the tightening strap using the strap fastener.

The present invention discloses a multifunctional De Quervain's brace. De Quervain's tenosynovitis is a disorder of the thumb and wrist tendons affected by incorrect muscle mechanics. The strain on the tendon occurs with movement due to the sharp wrist angle in ulnar deviation. The present invention changes the angle of pull of the tendons to provide some release in tension at the musculotendinous junction, thereby providing pain relief. As can be seen in FIGS. 1 through 6, the present invention comprises a thumb spica 1, a plurality of insert-receiving pockets 11, and a plurality of reinforcing inserts 18. The thumb spica 1 corresponds to the main structure of the present invention that is wrapped around the user's hand and wrist to position the plurality of insert-receiving pockets 11 and the corresponding plurality of reinforcing inserts 18 on the radial (thumb) side of the thumb spica 1. The plurality of insert-receiving pockets 11 and the plurality of reinforcing inserts 18 enable the adjustment of the restriction of the user's hand movements for different activities. For example, the present invention can be arranged into a static configuration for low-movement activities, such as when sleeping or lifting, while still providing a pull on the muscles to release the tension at the musculocutaneous junction, thereby treating the ailment and providing pain relief. In addition, the present invention can be arranged into a dynamic configuration for high-movement activities that allow for restrained movement during the day while modifying the angle of pull of the tendons and releasing the tension.

The general configuration of the aforementioned components enables the user to more comfortably perform everyday activities without suffering from pain due to hand and/or wrist issues. As can be seen in FIGS. 1 through 6, the thumb spica 1 is designed as a wearable device that can be removably attached by the user. The overall shape and size of the thumb spica 1 is designed to cover portions of the forearm, the wrist, and the hand while leaving the fingers, except the thumb, uncovered. Further, different sizes can be implemented for the thumb spica 1 to accommodate the user's body size. For example, the thumb spica 1 can be provided in a size range of small to extra-large and can be designed for right-hand and/or left-hand use. In addition, the thumb spica 1 can be made of a waterproof material to extend the functionality of the present invention. For example, the thumb spica 1 can be made of closed-cell-bonded neoprene, such as two-to-three-millimeter (mm) neoprene. However, different waterproof materials and thumb spica designs can be implemented to accommodate specific user needs.

As previously discussed, the thumb spica 1 matches the user's hand/wrist anatomy. As can be seen in FIGS. 1 through 6, the thumb spica 1 comprises a thumb sleeve 2 and a wrist-bracing wrap 3. The thumb sleeve 2 corresponds to the portion of the thumb spica 1 that covers the metacarpal and proximal phalanx portion of the thumb, while the wrist-bracing wrap 3 covers the forearm, the wrist, and portions of the hand adjacent to the wrist. Due to the elongated structure of the wrist-bracing wrap 3, the wrist-bracing wrap 3 comprises a proximal wrap edge 4, a distal wrap edge 5, a first lateral edge 6, a second lateral edge 7, an outer wrap surface 8, and an inner wrap surface 9. The proximal wrap edge 4 and the distal wrap edge 5 correspond to the shortest edges of the wrist-bracing wrap 3, while the first lateral edge 6 and the second lateral edge 7 correspond to the longest edges of the wrist-bracing wrap 3. Further, the outer wrap surface 8 corresponds to the surface exposed to the surroundings of the user's hand, while the inner wrap surface 9 corresponds to the surface exposed to the user's hand. In alternate embodiments, different designs can be implemented for the wrist-bracing wrap 3 to accommodate other features.

In the preferred embodiment, the present invention can be arranged as follows: the proximal wrap edge 4 and the distal wrap edge 5 are positioned opposite to each other across the wrist-bracing wrap 3 due to the overall length of the wrist-bracing wrap 3, as can be seen in FIGS. 1 through 6. Similarly, the first lateral edge 6 and the second lateral edge 7 are positioned opposite to each other across the wrist-bracing wrap 3 due to the overall width of the wrist-bracing wrap 3. Further, the first lateral edge 6 and the second lateral edge 7 are positioned in between the proximal wrap edge 4 and the distal wrap edge 5 due to the single solid structure of the wrist-bracing wrap 3. In addition, the thumb sleeve 2 is positioned adjacent to the distal wrap edge 5 and the first lateral edge 6 to accommodate the anatomical structure of the user's hand. The thumb sleeve 2 is also integrated through the wrap body to incorporate the thumb sleeve 2 into the wrist-bracing wrap 3. Further, the plurality of insert-receiving pockets 11 is distributed from the thumb sleeve 2 to the proximal wrap edge 4 so that the plurality of insert-receiving pockets 11 is positioned on the radial (thumb) side of the thumb spica 1. The plurality of insert-receiving pockets 11 is also mounted onto the outer wrap surface 8, adjacent to the first lateral edge 6, to secure the plurality of insert-receiving pockets 11 to the wrist-bracing wrap 3. Furthermore, each of the plurality of reinforcing inserts 18 is positioned within a corresponding pocket of the plurality of insert-receiving pockets 11 to secure each reinforcing insert inside the corresponding insert-receiving pocket. In other embodiments, different reinforcement features can be implemented to improve the functionality of the present invention.

As previously discussed, the plurality of insert-receiving pockets 11 and the plurality of reinforcing inserts 18 enable the present invention to be arranged into a static or dynamic configuration to accommodate different levels of movement according to user's tasks. As can be seen in FIGS. 1 through 6, in the preferred embodiment, each of the plurality of insert-receiving pockets 11 is a rectangular pocket large enough to accommodate the corresponding reinforcing insert. To provide the necessary reinforcement to the desired level of movement restraint, each of the plurality of reinforcing inserts 18 is preferably a rigid device that can be shaped to the contour of the radial side of the user's hand and wrist. For example, each of the plurality of reinforcing inserts 18 can be made of a thermoplastic material that can be shaped to the desired contour when heated up. Alternatively, each of the plurality of reinforcing inserts 18 can be made of a metal that can be shaped to the desired contour. In other embodiments, different materials and/or reinforcement devices can be implemented to accommodate the user's needs.

To facilitate the insertion and removal of the corresponding reinforcing insert, each of the plurality of insert-receiving pockets 11 is designed with a single opening. As can be seen in FIGS. 1 through 6, each of the plurality of insert-receiving pockets 11 may comprise a pocket body 12, a pocket open end 13, a pocket closed end 14, and a pocket-accessing tab 15. The pocket body 12 corresponds to the main structure of the corresponding insert-receiving pocket. The pocket open end 13 and the pocket closed end 14 correspond to the opposite terminal ends of each pocket body 12. The pocket-accessing tab 15 enables the adjustment of the movement restriction of the user's wrist/hand while wearing the present invention. Further, the pocket open end 13 and the pocket closed end 14 are positioned opposite to each other about the pocket body 12 due to length of each pocket body 12. In addition, the pocket-accessing tab 15 is externally connected to the pocket body 12, adjacent to the pocket open end 13, to secure the pocket-accessing tab 15 to the pocket body 12.

In the preferred embodiment, each of the plurality of insert-receiving pockets 11 further comprises a tab fastener 16 that allows each pocket-accessing tab 15 to be fastened to restrict the movement of the user's hand/wrist, as can be seen in FIGS. 1 through 6. In addition, the plurality of insert-receiving pockets 11 may comprise a plurality of remainder pockets 19 and a last pocket 20. The last pocket 20 corresponds to the insert-receiving pocket that is positioned adjacent to the proximal wrap edge 4. The last pocket 20 is arranged to position the corresponding reinforcing insert adjacent to the forearm. On other hand, the plurality of remainder pockets 19 preferably includes two remainder pockets positioned in between the last pocket 20 and the thumb sleeve 2. The first remainder pocket is positioned adjacent to the thumb sleeve 2 so that the corresponding reinforcing insert coincides with the metacarpal. In addition, the second remainder pocket is positioned in between the last pocket 20 and the first remainder pocket so that the corresponding reinforcing insert coincides with the trapezium.

As previously discussed, the present invention can be arranged into the static configuration to form a static splint. As can be seen in FIGS. 1 through 6, to arrange the present invention into the static configuration, the pocket-accessing tab 15 of the last pocket 20 is attached onto the outer wrap surface 8 by the tab fastener 16 of the last pocket 20. This pulls the last pocket 20 and the surrounding portions of the wrist-bracing wrap 3 towards proximal wrap edge 4. Further, the pocket-accessing tab 15 of an arbitrary pocket is attached onto an adjacent pocket by the tab fastener 16 of the arbitrary pocket, wherein the arbitrary pocket is any pocket from the plurality of remainder pockets 19, and wherein the adjacent pocket is from the plurality of insert-receiving pockets 11. In other words, the second remainder pocket and the surrounding portions of the wrist-bracing wrap 3 are pulled towards the last pocket 20 by the corresponding tab fastener 16. Similarly, the first remainder pocket and the surrounding portions of the wrist-bracing wrap 3 are pulled towards the second remainder pocket by the corresponding tab fastener 16. In the preferred embodiment, each tab fastener 16 is a hook-and-loop fastener, with the hook portion being implemented on the pocket-accessing tab 15, while the loop portion being implemented on the outside surface of the pocket body 12. The loop portion of the tab fastener 16 of the last pocket 20 is implemented on the outer wrap surface 8 adjacent to the pocket open end 13. In other embodiments, different types of fasteners can be implemented instead of a hook-and-loop fastener.

In the preferred embodiment, to arrange the present invention into the dynamic configuration, the desired pocket-accessing tab 15 is released by disengaging the corresponding tab fastener 16. By releasing the pocket-accessing tab 15 of each of the plurality of insert-receiving pockets 11, the user's hands are given greater freedom of movement for high-movement tasks. For example, during daytime exercise the released pocket-accessing tab 15 allows the patient to deviate pain free in an ulnar manner within the splint, thus allowing tendon to glide and the surrounding tissues to release. However, while moving, the tab fastener 16 on the pocket-accessing tab 15 may accidentally engage. As can be seen in FIGS. 1 through 6, to prevent this, each of the plurality of insert-receiving pockets 11 may further comprise a pair of support wires 17 for the pocket-accessing tab 15. The pair of support wires 17 make each pocket-accessing tab 15 stiff yet malleable so that each pocket-accessing tab 15 can be folded backwards in the dynamic configuration. So, the pair of support wires 17 is integrated into the pocket-accessing tab 15 to increase the structural strength of the corresponding pocket-accessing tab 15. In addition, the pair of support wires 17 is positioned opposite to each other about the pocket-accessing tab 15 so that the pair of support wires 17 line the pocket-accessing tab 15. In other embodiments, different mechanisms can be implemented to facilitate the malleability of the pocket-accessing tab 15.

As previously discussed, the present invention provides continuous pull on the hand/wrist muscles to release the tension at the musculocutaneous junction. As can be seen in FIGS. 1 through 6, the present invention may further comprise a tightening strap 21 that can be wrapped around the user's wrist. In addition, the wrist-bracing wrap 3 may further comprise a strap opening 10 that facilitates the wrapping of the tightening strap 21 while the user is wearing the present invention. The tightening strap 21 is preferably an elongated strap long enough to be wrapped around the user's wrist with a width of one and a half inches (in.). For example, the tightening strap 21 can start from the inside volar aspect of the distal forearm below the radial styloid, around the dorsum of the distal forearm above the wrist and wraps around the outside on the volar aspect to hook on the volar radial aspect of the wrist before the plurality of insert-receiving pockets 11.

As can be seen in FIGS. 1 through 6, the tightening strap 21 preferably comprises a fixed strap end 22, a free strap end 23, a first strap surface 24, and a second strap surface 25. The fixed strap end 22 and the free strap end 23 correspond to the terminal ends of the tightening strap 21, while the first strap surface 24 and the second strap surface 25 correspond to the opposite long surfaces of the tightening strap 21. To implement the tightening strap 21, the strap opening 10 traverses through the wrap body, adjacent to the second lateral edge 7, preferably coinciding with the ulnar head. On the other hand, the fixed strap end 22 is positioned adjacent to the thumb sleeve 2 coinciding with the inside volar radial aspect of the distal forearm below the radial styloid. In addition, the fixed strap end 22 is connected onto the inner wrap surface 9, adjacent to the first lateral edge 6, to secure the tightening strap 21 to the wrist-bracing wrap 3. Further, the first strap surface 24 is oriented towards the first lateral edge 6, while the second strap surface 25 is oriented towards the second lateral edge 7. This way, when the tightening strap 21 is wrapped around the user's wrist, the second strap surface 25 engages the user's skin. Further, the tightening strap 21 is positioned through the strap opening 10 so that the tightening strap 21 can be wrapped around the outside on the volar aspect. Furthermore, the free strap end 23 is positioned adjacent to the outer wrap surface 8 to hook on the volar radial aspect of the wrist.

As can be seen in FIGS. 1 through 6, to secure the tightening strap 21 around the user's wrist, the present invention may further comprise a strap fastener 26. The strap fastener 26 helps secure the tightening strap 21 in place when the user is wearing the present invention. The strap fastener 26 comprises a first fastener piece 27 and a second fastener piece 28 corresponding to two fastener pieces that can be selectively engaged to each other. In the preferred embodiment, the first fastener piece 27 is mounted onto the second strap surface 25, adjacent to the free strap end 23, to secure the first fastener piece 27 to the tightening strap 21. On the other hand, the second fastener piece 28 is positioned adjacent to the thumb sleeve 2 and mounted onto the outer wrap surface 8, offset from the first lateral edge 6 and offset from the second lateral edge 7. This way, the second fastener piece 28 is positioned adjacent to the plurality of insert-receiving pockets 11 to coincide with the volar radial aspect of the wrist. The strap fastener 26 is preferably a hook-and-loop fastener, with the hook portion corresponding to the first fastener piece 27, and the loop portion corresponding to the second fastener piece 28. In other embodiments, different fasteners can be implemented for the tightening strap 21.

For the tightening strap 21 to hug and stick to the dorsal aspect of the skin, the present invention may further comprise a gripping feature 29 and a feature fastener 30, as can be seen in FIGS. 1 through 6. The gripping feature 29 allows the dorsal aspect of the skin to be pulled in an ulnar manner, thereby changing the angle and providing a gentle lengthening and providing release of the tissues. The feature fastener 30 allows the removable attachment of the gripping feature 29 to the tightening strap 21. So, the gripping feature 29 can be attached onto the second strap surface 25 by the feature fastener 30, adjacent to the fixed strap end 22. Like the strap fastener 26, the feature fastener 30 can be a hook-and-loop fastener that can engage with the loop portion of the strap fastener 26. In addition, the gripping feature 29 is preferably made of a silicone material of one and half inches in width and three inches in length. Silicone assists with the release of tissue on the back of the forearm and can also be used to reduce spasticity and provide proprioceptive feedback. The gripping feature 29 allows increased sensory feedback from silicone so improves compliance. In addition, the gripping feature 29 assists with management of scar by the application of pressure and gentle stretch on the dorsum of the wrist/forearm and the thumb area. The gripping feature 29 is removable so that the position of the gripping feature 29 can be adjusted along the tightening strap 21 and enables the gripping feature 29 to be easily cleaned. In other embodiments, different gripping materials can be utilized as well as fasteners.

As can be seen in FIGS. 1 through 6, to facilitate the fastening of the wrist-bracing wrap 3 when the user is wearing the present invention, the present invention may further comprise a wrap fastener 31. The wrap fastener 31 enables the wrist-bracing wrap 3 to be locked in place so that the user can comfortably perform the desired actions without risk. Like the strap fastener 26, the wrap fastener 31 comprises a first fastening strip 32 and a second fastening strip 33. The first fastening strip 32 and the second fastening strip 33 correspond to two fastener pieces that can be selectively engaged to each other. The first fastening strip 32 is preferably mounted onto the outer wrap surface 8 along the first lateral edge 6, while the second fastening strip 33 is mounted onto the inner wrap surface 9 along the second lateral edge 7. This way, after the user inserts the thumb into the thumb sleeve 2, the user wraps second lateral edge 7 until the second fastening strip 33 coincides with the first fastening strip 32. Then, the second fastening strip 33 is engaged to the first fastening strip 32 to lock the wrist-bracing wrap 3 in place. Further, the wrap fastener 31 is preferably a hook-and-loop fastener, with the hook portion being the second fastening strip 33, and the loop portion being the first fastening strip 32. In other embodiments, different types of fasteners can be implemented for the wrap fastener 31.

Although the invention has been explained in relation to its preferred embodiment, it is to be understood that many other possible modifications and variations can be made without departing from the spirit and scope of the invention.

What is claimed is:

1. A multifunctional De Quervain's brace comprising:
a thumb spica;
a plurality of insert-receiving pockets;
a plurality of reinforcing inserts;
the thumb spica comprising a thumb sleeve and a wrist-bracing wrap;
the wrist-bracing wrap comprising a proximal wrap edge, a distal wrap edge, a first lateral edge, a second lateral edge, an outer wrap surface, and an inner wrap surface;
each of the plurality of insert-receiving pockets comprising a pocket body, a pocket open end, a pocket closed end, a pocket-accessing tab, and a tab fastener;
the plurality of insert-receiving pockets comprising a plurality of remainder pockets and a last pocket;
the proximal wrap edge and the distal wrap edge being positioned opposite to each other across the wrist-bracing wrap;
the first lateral edge and the second lateral edge being positioned opposite to each other across the wrist-bracing wrap;
the first lateral edge and the second lateral edge being positioned in between the proximal wrap edge and the distal wrap edge;
the thumb sleeve being positioned adjacent to the distal wrap edge and the first lateral edge;
the thumb sleeve being integrated through the wrap body;
the plurality of insert-receiving pockets being distributed from the thumb sleeve to the proximal wrap edge;
the plurality of insert-receiving pockets being mounted onto the outer wrap surface, adjacent to the first lateral edge; and
each of the plurality of reinforcing inserts being positioned within a corresponding pocket of the plurality of insert-receiving pockets;
the pocket open end and the pocket closed end being positioned opposite to each other about the pocket body;
the pocket-accessing tab being externally connected to the pocket body, adjacent to the pocket open end;
the last pocket being positioned adjacent to the proximal wrap edge;
the plurality of remainder pockets being positioned in between the last pocket and the thumb sleeve;

the pocket-accessing tab of the last pocket being attached onto the outer wrap surface by the tab fastener of the last pocket; and the pocket-accessing tab of an arbitrary pocket being attached onto an adjacent pocket by the tab fastener of the arbitrary pocket, wherein the arbitrary pocket is any pocket from the plurality of remainder pockets, and wherein the adjacent pocket is from the plurality of insert-receiving pockets.

2. The multifunctional De Quervain's brace as claimed in claim 1, wherein each of the plurality of reinforcing inserts is made of a thermoplastic material.

3. The multifunctional De Quervain's brace as claimed in claim 1, wherein each of the plurality of reinforcing inserts is made of a metal.

4. The multifunctional De Quervain's brace as claimed in claim 1, wherein the tab fastener is a hook-and-loop fastener.

5. The multifunctional De Quervain's brace as claimed in claim 1 further comprising:

each of the plurality of insert-receiving pockets further comprising a pair of support wires;

the pair of support wires being integrated into the pocket-accessing tab; and the pair of support wires being positioned opposite to each other about the pocket-accessing tab.

6. The multifunctional De Quervain's brace as claimed in claim 1 comprising:

a tightening strap;

the wrist-bracing wrap further comprising a strap opening;

the tightening strap comprising a fixed strap end, a free strap end, a first strap surface, and a second strap surface;

the strap opening traversing through the wrap body, adjacent to the second lateral edge;

the fixed strap end being positioned adjacent to the thumb sleeve;

the fixed strap end being connected onto the inner wrap surface, adjacent to the first lateral edge;

the first strap surface being oriented towards the first lateral edge;

the second strap surface being oriented towards the second lateral edge;

the tightening strap being positioned through the strap opening; and the free strap end being positioned adjacent to the outer wrap surface.

7. The multifunctional De Quervain's brace as claimed in claim 6 further comprising:

a strap fastener;

the strap fastener comprising a first fastener piece and a second fastener piece;

the first fastener piece being mounted onto the second strap surface, adjacent to the free strap end;

the second fastener piece being positioned adjacent to the thumb sleeve; and the second fastener piece being mounted onto the outer wrap surface, offset from the first lateral edge and offset from the second lateral edge.

8. The multifunctional De Quervain's brace as claimed in claim 7, wherein the strap fastener is a hook-and-loop fastener.

9. The multifunctional De Quervain's brace as claimed in claim 6 further comprising:

a gripping feature;

a feature fastener; and the gripping feature being attached onto the second strap surface by the feature fastener, adjacent to the fixed strap end.

10. The multifunctional De Quervain's brace as claimed in claim 9, wherein the gripping feature is made of a silicone material.

11. The multifunctional De Quervain's brace as claimed in claim 9, wherein the feature fastener is a hook-and-loop fastener.

12. The multifunctional De Quervain's brace as claimed in claim 1 further comprising:

a wrap fastener;

the wrap fastener comprising a first fastening strip and a second fastening strip;

the first fastening strip being mounted onto the outer wrap surface along the first lateral edge; and the second fastening strip being mounted onto the inner wrap surface along the second lateral edge.

13. The multifunctional De Quervain's brace as claimed in claim 12, wherein the wrap fastener is a hook-and-loop fastener.

* * * * *